US012600697B2

(12) United States Patent
Overholt et al.

(10) Patent No.: US 12,600,697 B2
(45) Date of Patent: Apr. 14, 2026

(54) COMPOSITIONS AND METHODS FOR REMOVAL OF N-METHYL-2-PYRROLIDONE (NMP) DEGRADATION PRODUCTS AND OTHER FOULANTS FROM NMP PURIFICATION SYSTEMS

(71) Applicant: Refined Technologies, Inc., Spring, TX (US)

(72) Inventors: Jerrod Overholt, San Pedro, CA (US); Sean E. Sears, The Woodlands, TX (US)

(73) Assignee: Refined Technologies, Inc., Spring, TX (US)

( * ) Notice: Subject to any disclaimer, the term of this patent is extended or adjusted under 35 U.S.C. 154(b) by 415 days.

(21) Appl. No.: 18/562,589

(22) PCT Filed: May 25, 2022

(86) PCT No.: PCT/US2022/030878
§ 371 (c)(1),
(2) Date: Nov. 20, 2023

(87) PCT Pub. No.: WO2022/251327
PCT Pub. Date: Dec. 1, 2022

(65) Prior Publication Data
US 2024/0132446 A1 Apr. 25, 2024

Related U.S. Application Data

(60) Provisional application No. 63/193,438, filed on May 26, 2021.

(51) Int. Cl.
| | |
|---|---|
| *C07D 201/16* | (2006.01) |
| *B01D 3/14* | (2006.01) |
| *C07D 207/267* | (2006.01) |

(52) U.S. Cl.
CPC ............ *C07D 201/16* (2013.01); *B01D 3/14* (2013.01); *C07D 207/267* (2013.01)

(58) Field of Classification Search
CPC .......................... C07D 207/267; C07D 201/16
See application file for complete search history.

(56) References Cited

U.S. PATENT DOCUMENTS

| | | |
|---|---|---|
| 2005/0288318 A1 | 12/2005 | Bourrie et al. |
| 2012/0241307 A1 | 9/2012 | Miyata et al. |
| 2013/0210692 A1 | 8/2013 | Gutowski et al. |

OTHER PUBLICATIONS

International Search Report mailed Oct. 5, 2022 and issued in PCT counterpart application No. PCT/US2022/030878. 12 pages.

*Primary Examiner* — Jonathan Luke Pilcher
(74) *Attorney, Agent, or Firm* — Blank Rome LLP

(57) ABSTRACT

Methods of cleaning an N-methyl-2-pyrrolidone (NMP) purification and recovery system having an NMP-containing chemical waste stream, a separation tower fluidically coupled with the chemical waste stream, a reflux drum fluidically coupled with an upper section of the separation tower, a reboiler fluidically coupled with a lower section of the separation tower, and a purified NMP stream fluidically coupled with the reboiler. The methods include injecting a cleaning solution into the reflux drum and the reboiler with an amount of the cleaning solution sufficient to at least substantially fill the reflux drum and the reboiler, the cleaning solution comprising a solvent having a primary amine and a hydroxyl group, circulating the cleaning solution through at least the separation tower, the reflux drum, the reboiler for a period of time to solubilize foulants contained within the system, and draining the cleaning solution having foulants solubilized therein from the system.

15 Claims, 6 Drawing Sheets

COMPOSITIONS AND METHODS FOR REMOVAL OF N-METHYL-2-PYRROLIDONE (NMP) DEGRADATION PRODUCTS AND OTHER FOULANTS FROM NMP PURIFICATION SYSTEMS

CROSS REFERENCE TO RELATED APPLICATION

This application is a national stage of International Application No. PCT/US2022/030878, filed May 25, 2022, which claims the benefit of U.S. Provisional Application No. 63/193,438, filed May 26, 2021, the entire contents of which are incorporated herein by reference.

FIELD OF THE INVENTION

The present invention relates to compositions and methods for removing N-methyl-2-pyrrolidone (NMP) degradation products and other foulants from systems designed to purify and recover NMP from chemical waste streams produced during industrial processes.

BACKGROUND OF THE DISCLOSURE

N-methyl-2-pyrrolidone (NMP) is common organic solvent used in a variety of industrial processes. For example, NMP is used to recover certain hydrocarbons generated in the processing of petrochemicals, such as the recovery of 1,3-butadiene and acetylene. NMP is also used to absorb hydrogen sulfide from sour gas and hydrodesulfurization facilities. NMP has various uses as a solvent for the surface treatment of textiles, resins, and metal-coated plastics. NMP is also a very effective solvent in paint stripping applications. NMP is also used heavily in lithium-ion battery fabrication as a solvent for electrode preparation.

While NMP is a valuable solvent for various applications, the use thereof does present certain risks to the environment, occupational workers and the general population. As such, various industries undertake extensive efforts to purify chemical waste streams containing NMP and recover purified NMP from said waste streams for subsequent sale and/or re-use. An exemplary prior art system for the treatment of chemical waste streams for the purification and recovery of N-methyl-2-pyrrolidone (NMP) therefrom is illustrated in FIG. 1.

Over time, the internal surfaces of various components of such prior art NMP purification/recovery systems become caked with impurities such as NMP degradation products, carbon deposits, and other industrial process foulants. The presence of these materials limits the efficiency of such systems to effectively purify and recover NMP. Presently, to clean the internal surfaces of NMP purification/recovery systems, one has to disconnect all system components from connective piping and subject the system components and connective piping to hydraulic water blasting at pressures ranging from about 6,000 to about 30,000 psi. The hydraulic water blasting process is not only laborious and time consuming, but also results in extended periods of time where the NMP purification/recovery system is not in service, which leads to an accumulation of NMP-containing chemical waste streams that must be safely stored and maintained.

SUMMARY OF THE DISCLOSURE

According to various aspects of the disclosure, methods of and compositions for cleaning an N-methyl-2-pyrrolidone (NMP) purification and recovery system, where the system comprises an NMP-containing chemical waste stream, a separation tower fluidically coupled with the chemical waste stream, a reflux drum fluidically coupled with an upper section of the separation tower, a reboiler fluidically coupled with a lower section of the separation tower, and a purified NMP stream fluidically coupled with the reboiler, are described.

According to various aspects of the disclosure, a first embodiment is directed to a method comprises injecting a cleaning solution into the reflux drum and the reboiler with an amount of the cleaning solution sufficient to at least substantially fill the reflux drum and the reboiler, the cleaning solution comprising a solvent having a primary amine and a hydroxyl group; circulating the cleaning solution through at least the separation tower, the reflux drum, the reboiler for a period of time to solubilize foulants contained within the system; and draining the cleaning solution having foulants solubilized therein from the system.

According to various aspects of the disclosure, a second embodiment is directed to a method according to the first embodiment, further comprising injecting a cleaning solution into the reflux drum and the reboiler with an amount of the cleaning solution sufficient to at least substantially fill a lower portion of the separation tower.

According to various aspects of the disclosure, a third embodiment is directed to a method according to the first or second embodiments, wherein circulating the cleaning solution is facilitated by a bottoms pump fluidically coupled with the lower section of the separation tower and the reboiler and an overhead pump fluidically coupled with the section of the separation tower and the reflux drum.

According to various aspects of the disclosure, a fourth embodiment is directed to a method according to any one of the first through third embodiments, wherein a vapor return from the reboiler to the lower section of the separation tower is at ambient temperature prior to injecting the cleaning solution.

According to various aspects of the disclosure, a fifth embodiment is directed to a method according to any one of the first through third embodiments, wherein a vapor return from the reboiler to the lower section of the separation tower is at an operating temperature of between about 38° C. and about 55° C. prior to injecting the cleaning solution.

According to various aspects of the disclosure, a sixth embodiment is directed to a method according to any one of the first through third embodiments, wherein a vapor return from the reboiler to the lower section of the separation tower is at an operating temperature of between ambient temperature and about 55° C. prior to injecting the cleaning solution.

According to various aspects of the disclosure, a seventh embodiment is directed to a method according to any one of the first through sixth embodiments, wherein a vapor return from the reboiler to the lower section of the separation tower is at an operating temperature of between about 38° C. and about 55° C. during circulation of the cleaning solution.

According to various aspects of the disclosure, an eighth embodiment is directed to a method according to any one of the first through seventh embodiments, wherein the solvent is a glycolamine.

According to various aspects of the disclosure, a ninth embodiment is directed to a method according to any one of the first through seventh embodiments, wherein the solvent is diglycolamine.

According to various aspects of the disclosure, a tenth embodiment is directed to a method according to any one of the first through seventh embodiments, wherein the solvent is one or more of (2-aminoethoxy)ethanol, 2-[2-(2-amino-ethoxy)ethoxy]ethanol, 2-(2-(2-(2-aminoethoxy)ethoxy) ethoxy)ethanol, 2-(2-amino-1-methylethoxy)ethanol, 2-[(3-aminopropyl)(ethyl)amino]ethanol, 2-(2-aminoethylamino) ethanol, 3-[(2-aminoethyl)amino]-1-propanol, and 2-(2-amino-1,1-dimethyl-ethylamino)ethanol.

According to various aspects of the disclosure, an eleventh embodiment is directed to a method according to any one of the first through tenth embodiments, wherein the cleaning solution has a solvent-to-water volumetric ratio ranging from about 50:50 to about 100:0.

According to various aspects of the disclosure, a twelfth embodiment is directed to a method according to any one of the first through tenth embodiments, wherein the cleaning solution has a water-to-solvent volumetric ratio ranging from about 80:20 to about 50.1:49.9.

According to various aspects of the disclosure, a thirteenth embodiment is directed to a method according to any one of the first through twelfth embodiments, wherein the cleaning solution is circulated for a period of time ranging from about 30 minutes to about 4 hours.

According to various aspects of the disclosure, a fourteenth embodiment is directed to a method according to any one of the first through twelfth embodiments, wherein the cleaning solution is circulated for a period of time ranging from about 1 hour to about 3 hours.

According to various aspects of the disclosure, a fifteenth embodiment is directed to a method according to any one of the first through twelfth embodiments, wherein the cleaning solution is circulated for a period of time of about 2 hours.

According to various aspects of the disclosure, a sixteenth embodiment is directed to an NMP purification and recovery system cleaning solution comprising a solvent having a primary amine and a hydroxyl group.

According to various aspects of the disclosure, a seventeenth embodiment is directed to an NMP purification and recovery system cleaning solution according to the sixteenth embodiment, wherein the solvent is a glycolamine.

According to various aspects of the disclosure, an eighteenth embodiment is directed to an NMP purification and recovery system cleaning solution according to the sixteenth embodiment, wherein the solvent is diglycolamine.

According to various aspects of the disclosure, a nineteenth embodiment is directed to an NMP purification and recovery system cleaning solution according to the sixteenth embodiment, wherein the solvent is one or more of (2-aminoethoxy)ethanol, 2-[2-(2-aminoethoxy)ethoxy]ethanol, 2-(2-(2-(2-aminoethoxy)ethoxy)ethoxy)ethanol, 2-(2-amino-1-methylethoxy)ethanol, 2-[(3-aminopropyl)(ethyl) amino]ethanol, 2-(2-aminoethylamino)ethanol, 3-[(2-aminoethyl)amino]-1-propanol, and 2-(2-amino-1,1-dimethyl-ethylamino)ethanol.

According to various aspects of the disclosure, a twentieth embodiment is directed to an NMP purification and recovery system cleaning solution according to any one of the sixteenth through nineteenth embodiments, further comprising water.

According to various aspects of the disclosure, a twenty-first embodiment is directed to an NMP purification and recovery system cleaning solution according to the twentieth embodiment, wherein the cleaning solution has a solvent-to-water volumetric ratio ranging from about 50:50 to about 100:0.

According to various aspects of the disclosure, a twenty-second embodiment is directed to an NMP purification and recovery system cleaning solution according to the twentieth embodiment, wherein the cleaning solution has a water-to-solvent volumetric ratio ranging from about 80:20 to about 50.1:49.9.

DETAILED DESCRIPTION

Figure 1:
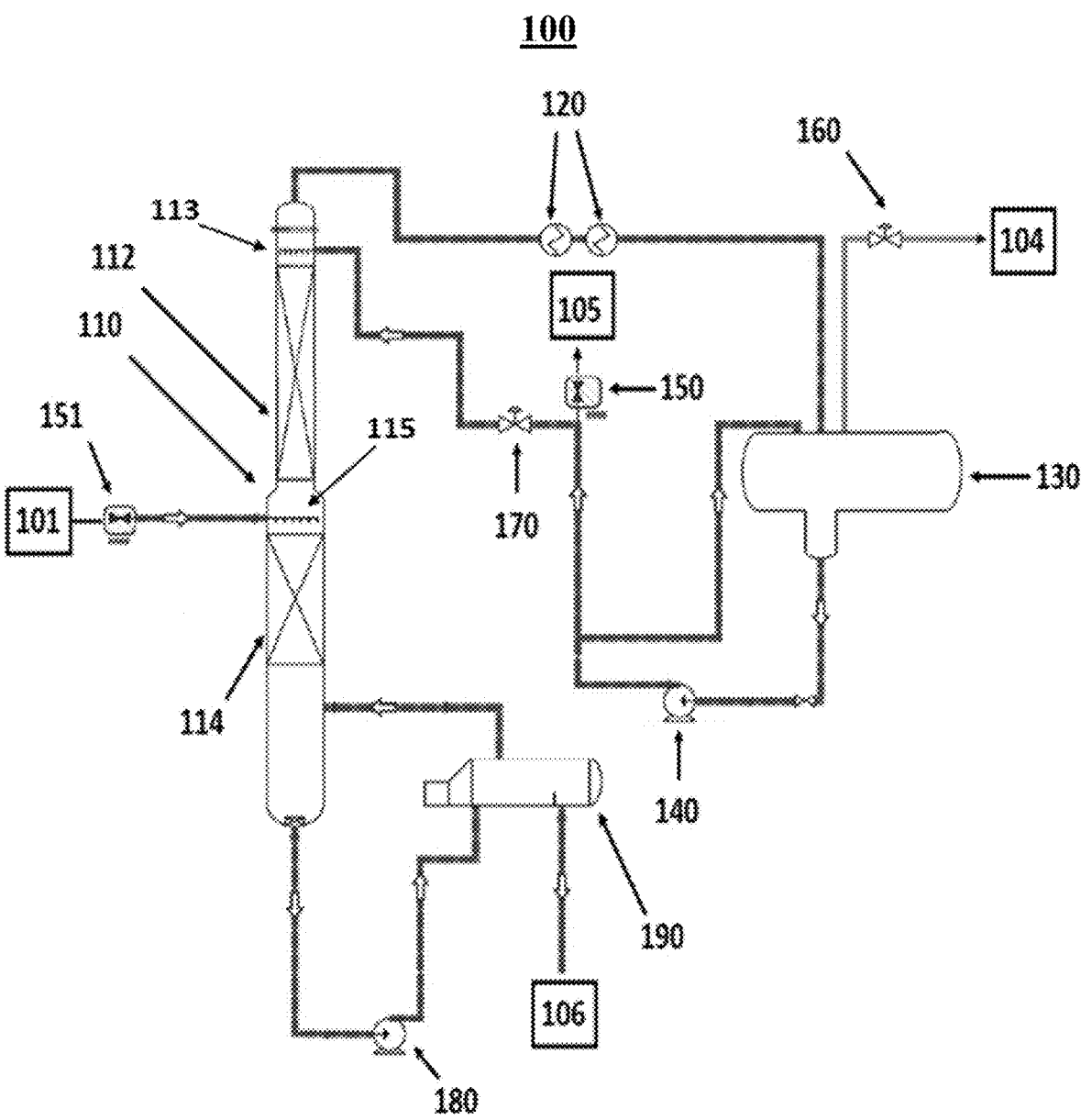
FIG. 1 is a schematic illustration of a prior art system for the treatment of N-methyl-2-pyrrolidone (NMP)-containing chemical waste streams for the purification and recovery of NMP therefrom.

The following description of the embodiments is merely exemplary in nature and is in no way intended to limit the subject matter of the present disclosure, their application, or uses.

As used throughout, ranges are used as shorthand for describing each and every value that is within the range. Any value within the range can be selected as the terminus of the range. Unless otherwise specified, all percentages and amounts expressed herein and elsewhere in the specification should be understood to refer to percentages by weight.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent, alternatively ±5 percent, alternatively ±1 percent, alternatively ±0.5 percent, and alternatively ±0.1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "includes" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

For the purposes of this specification and appended claims, the term "coupled" refers to the linking or connection of two objects. The coupling can be permanent or reversible. The coupling can be direct or indirect. An indirect coupling includes linking or connecting two objects through one or more intermediary objects. The term "fluidically coupled" refers to the linking or connection of two objects to allow for the transmission of a fluid (e.g., a liquid, gas or vapor) therebetween. The term "substantially", as used herein, is defined to be essentially conforming to the particular dimension, shape or other word that substantially modifies, such that the component need not be exact. For example, substantially cylindrical means that the object resembles a cylinder, but can have one or more deviations from a true cylinder.

FIG. 1 is a schematic illustration showing a prior art system 100 for the treatment of a chemical waste stream containing N-methyl-2-pyrrolidone (NMP) for the purpose of purifying and recovering the NMP from the chemical waste stream. One of ordinary skill in the art will appreciate that the system 100 is exemplary in nature and may include additional elements and/or configurational variations.

The system 100 generally includes an NMP-containing waste source 101, a separation tower 110 (with upper and lower packing beds 112, 114 respectively, and distribution manifold/spray headers 113, 115), coolers 120, a reflux drum 130, an overhead pump 140, isolation valves 150 and 151, a pressure controller 160, vacuum generating equipment 104, a reflux valve 170, a bottoms pump 180, a reboiler 190, an NMP-deficient waste stream 105 (which may contain, for example, a relatively small amount of impure NMP and other contaminants such as water), and a purified NMP stream 106. In use, the NMP-containing waste source 101 is introduced into the separation tower 110 via metal piping. The separation tower 110 heats the NMP-containing waste to a temperature below the boiling point of NMP (202° C.) but above the boiling point of other components of the NMP-containing waste such as, for example, water and alcoholic or other organic solvents (hereinafter "waste materials"), to result in a waste material vapor and an NMP-rich solution.

The waste materials vapor traverses packing bed 112 and exits the top of the separation tower 110, and is transmitted to coolers 120 to convert the waste materials vapor to a waste materials solution. The waste materials solution is then transmitted to the reflux drum 130. The waste materials solution is then transmitted from the reflux drum 130 to either the NMP-deficient waste stream 105 by actuating the isolation valve 150 from a closed position to an open position or is transmitted to the distribution manifold/spray header 113 by actuating the reflux valve 170 from a closed position to an open position.

The NMP-rich solution traverses packing bed 114 and exits the bottom of the separation tower 110, and is transmitted to the reboiler 190 with the assistance of the bottoms pump 180. The reboiler 190 heats the NMP-rich solution to a temperature below the boiling point of NMP but above the boiling point of waste materials still remaining in the NMP-rich solution to vaporize said waste materials. Vaporized waste materials are transmitted from the reboiler 190 to the separation tower 110 and purified NMP exits the reboiler 190 via purified NMP stream 106.

Over time, systems such as system 100 will suffer from reduced NMP recovery efficiencies due to the build-up of various impurities (for example, NMP degradation products, organic solvents and degradation products thereof, etc.) of internal surfaces of components of the system such as the separation tower 110 and its packing beds 112 and 114, the reflux drum 130, the overhead pump 140, the bottoms pump 180, the reboiler 190 and the metal piping coupling the various system components together. As discussed above, the prior art methods for removing impurities caked on internal surfaces of the system components are laborious and time intensive and result in extended shut-down times of the system. In accordance with various aspects of the disclosure, the inventors of the instant application have discovered systems, methods and compositions for cleaning the internal surfaces of systems, for the treatment of a chemical waste streams containing NMP for the purpose of purifying and recovering the NMP from the chemical waste stream, that are substantial improvements over the prior art methods.

Figure 2:
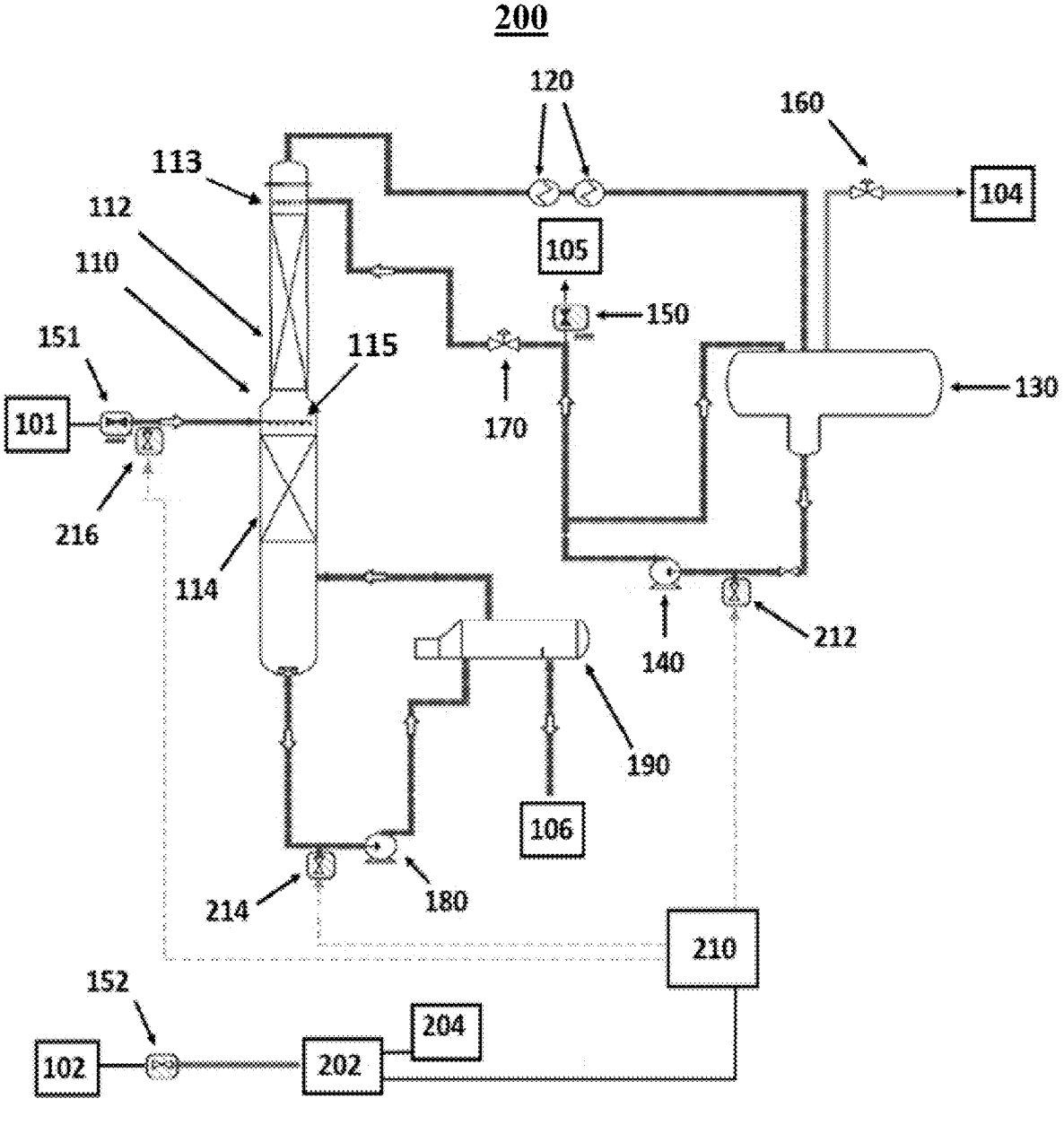
FIG. 2 is a schematic illustration of an inventive modified system, of the prior art system shown in FIG. 1, according to various aspects of the present disclosure for cleaning internal surfaces and components of the system.

FIG. 2 is a schematic illustration of an inventive modified system of system 200 in accordance with various aspects of the present disclosure. The modified system includes all of the components of system 100 (which is exemplary in nature and may include additional elements and/or configurational variations). In addition, system 200 includes a water source 102 and a cleaning solvent source 204 coupled with flow meters 202. In some instances, transmission of water from water source 102 to the flow meters can be controlled by a valve 152. Water, from the water source 102, and a cleaning solvent, from the cleaning solvent source 204, are combined in controlled amounts via the flow meters 202 and mix to form a cleaning solution while travelling in connective piping or hoses from the flow meters 202 to a set of flow valves 210. The flow valves 210 can be transitioned from a closed position to an open position to transmit the cleaning solution via connective piping or hoses to one or more of injection valves 212, 214 and 216.

As shown in FIG. 2, injection valve 212 allows for injection of the cleaning solution in connective piping coupling the reflux drum 130 with the overhead pump 140, injection valve 214 allows for injection of the cleaning solution in connective piping coupling the bottom of the tower 110 with the bottoms pump 180, and injection valve 215 allows for injection of the cleaning solution in connective piping coupling the NMP-containing waste source 101 to the distribution manifold/spray header 115 of the tower 110. In some instances, injection valve 216 may be omitted. In some instances, the system may include additional injection valves. For example, in some instances, flow valves 210 may be coupled via connective piping or hoses to an injection valve (not shown) located at connective piping coupling the top of the tower 110 to the coolers 120.

In accordance with various aspects of the disclosure, the cleaning solvent comprises, consists essentially of, or consists of an amine-based solvent. In some instances, the cleaning solvent comprises, consists essentially of, or consists of a solvent having a primary amine and a hydroxyl group as the amine-based solvent. In some instances, the cleaning solvent comprises, consists essentially of, or consists of a glycolamine as the amine-based solvent. Examples of suitable solvents having a primary amine and a hydroxyl group include, but are not limited to, 2-(2-aminoethoxy) ethanol (diglycolamine, or "DGA"), 2-[2-(2-aminoethoxy) ethoxy]ethanol (Triglycolamine, or "TGA"), 2-(2-(2-(2-aminoethoxy)ethoxy)ethoxy)ethanol, 2-(2-amino-1-methylethoxy)ethanol, 2-[(3-aminopropyl)(ethyl)amino] ethanol, 2-(2-aminoethylamino)ethanol, 3-[(2-aminoethyl) amino]-1-propanol, 2-(2-amino-1,1-dimethyl-ethylamino) ethanol. In some instances, the solvent may be a mixture of two or more amine-based solvents. In some instances, the solvent may be a mixture of two or more solvents, each having a primary amine and a hydroxyl group. In some instances, the use of DGA, alone or in combination with one or more additional amine-based solvents is preferred.

Cleaning solutions according to various aspects of the present disclosure comprise, consist essentially of, or consist of an amine-based solvent or a combination of an amine-based solvent and water. In some instances, the cleaning solution can have a solvent-to-water volumetric ratio of 50:50. In some instances, the cleaning solution can have a solvent-to-water volumetric ratio of 100:0. In some instances, the cleaning solution can have a solvent-to-water volumetric ratio ranging from about 50:50 to about 100:0. In some instances, the cleaning solution can have a solvent-to-water volumetric ratio ranging from about 50:50 to about 99:1, alternatively from about 50:50 to about 95:5, alternatively from about 50:50 to about 90:10, alternatively from about 50:50 to about 85:15, alternatively from 50:50 to about 80:20, alternatively from about 50:50 to about 75:25, alternatively from about 50:50 to about 70:30, alternatively from about 50:50 to about 65:35, alternatively from about 50:50 to about 60:40, alternatively from about 50:50 to about 55:45, and alternatively from about 50:50 to about 52.5:47.5. In some instances, the cleaning solution can have a solvent-to-water volumetric ratio ranging from about 51:49 to about 100:0, alternatively from about 55:45 to about 100:0, alternatively from 60:40 to about 100:0, alternatively from 65:35 to about 100:0, alternatively from 70:30 to about 100:0, alternatively from 75:25 to about 100:0, alternatively from 80:20 to about 100:0, alternatively from 85:15 to about 100:0, alternatively from 90:10 to about 100:0, alternatively from 95:5 to about 100:0, and alternatively from 97.5:2.5 to about 100:0.

In some instances, cleaning solutions according to various aspects of the present disclosure comprise, consist essentially of, or consist of can have water as the solvent and the amine-based solvent as the solute. In such instances, the cleaning solution can have a solvent (water)-to-solute (amine) volumetric ratio ranging from about 80:20 to about 50.1:49.9, alternatively from about 75:25 to about 50.1:49.9, alternatively from about 70:30 to about 50.1:49.9, alternatively from about 65:35 to about 50.1:49.9, alternatively from about 60:40 to about 50.1:49.9, alternatively from about 55:45 to about 50.1:49.9, alternatively from about 57.5:47.5 to about 50.1:49.9, and alternatively from about 51:49 to about 50.1:49.9.

Referring again to FIGS. 1-2, a method according to various aspects of the disclosure for cleaning the internal surfaces of a system for the treatment of N-methyl-2-pyrrolidone (NMP)-containing chemical waste streams, such as system 100, can proceed as follows. In a first step, cleaning solution is prepared by injecting and in-line mixing water, from water source 102, and a cleaning solvent, from cleaning solvent source 204, in a connective piping from flow meters 202 to form a cleaning solution. The connective piping transmits the cleaning solution from the flow meters 202 to flow valves 210. The resulting cleaning solution can have any ratio of cleaning solvent and water as discussed above.

In some instances, in the first step, water flow from water source 102 to the flow meters 202 can be terminated by closing valve 152, resulting in the transmission of only cleaning solvent from cleaning solvent source 204 to flow valves 210 via flow meters 202.

In a second step, the flow valves 210 are transitioned from a closed position to an open position to transmit the cleaning solution to at least injection valves 212 and 214, and optionally injection valve 216.

In a third step, the cleaning solution is injected into reflux drum 130 from injection valve 212 via the overhead pump 140 and associated connective piping, cleaning solution is injected into reboiler 190 from injection valve 214 via the bottoms pump 180 and associated connective piping, and optionally cleaning solution is injected from injection valve 216 into tower 110 via associated connective piping coupled with distribution manifold/spray header 115. Injection of the cleaning solution is performed until the reflux drum 130, reboiler 190 and optionally a bottom portion of tower 110 are filled or substantially filled with cleaning solution. The term "substantially filled" as used herein, means at least 70% filled, preferably at least 80% filled, more preferably at least 85% filled, even more preferably at least 90% filled, and even more preferably at least 95% filled.

In the third step, injection of the cleaning solution can be performed at an injection rate ranging from about 10 gallons per minute (GPM) to about 200 GPM. In some instances, injection of the cleaning solution can be performed at an injection rate ranging from about 20 GPM to about 180 GPM, alternatively from about 30 GPM to about 170 GPM, alternatively from about 40 GPM to about 160 GPM, alternatively from about 50 GPM to about 150 GPM, alternatively from about 60 GPM to about 140 GPM, alternatively from about 70 GPM to about 130 GPM, alternatively from about 80 GPM to about 120 GPM, alternatively from about 90 GPM to about 110 GPM, alternatively from about 95 GPM to about 105 GPM, alternatively about 100 GPM. In some instances, an injection rate of about 100 GPM is preferred.

In some instances, the vapor return from the reboiler 190 to the tower 110 is at ambient temperature during injection of the cleaning solution and filling of the reflux drum 130, reboiler 190 and optional bottom portion of tower 110. In some instances, the vapor return from the reboiler 190 to the tower 110 is heated to an operational temperature of about 38° C. prior to beginning injection of the cleaning solution. In some instances, the vapor return from the reboiler 190 to the tower 110 is heated to an operational temperature of about 55° C. prior to beginning injection of the cleaning solution. In some instances, the vapor return from the reboiler 190 to the tower 110 is to an operational temperature between about 38° C. and about 55° C. prior to beginning injection of the cleaning solution.

In some instances, the vapor return from the reboiler 190 to the tower 110 is at ambient temperature during injection of the cleaning solution and is raised to an operational temperature ranging from about 38° C. and about 55° C. during said injection. In such instances, the temperature may be raised incrementally or continuously over time. For example, the temperature may be raised incrementally or continuously from ambient to an operational temperature ranging from about 38° C. and about 55° C. in increments of about 1° C. to about 10° C., alternatively increments of about 2.5° C. to about 7.5° C., and alternatively increments of about 5° C. every 5 minutes to about every 30 minutes, alternatively about every 10 minutes to about 20 minutes, and alternatively about every 15 minutes.

In a fourth step, bottoms pump 180 and overhead pump 140 are activated and the cleaning solution is circulated throughout the system components (for example, the separation tower 110 and upper and lower packing beds 112, 114, and distribution manifold/spray headers 113, 115, reflux drum 130, overhead pump 140, pressure controller 160, reflux valve 170, bottoms pump 180, and reboiler 190) and associated connective piping at the operational temperature. In some instances, circulation takes place over a period of time ranging from about 30 minutes to about 4 hours. Preferably, circulation takes place over a period of time ranging from about 45 minutes to about 3.5 hours, more preferably over a period of time ranging from about 1 hour to about 3 hours, even more preferably over a period of time ranging from about 1.5 to about 2.5 hours, and even more preferably over a period of time of about 2 hours. During this circulation period, aliquots of the cleaning solution may be removed from the system to assess the amount of foulant that has been solubilized by the cleaning solution over time.

In a fifth step, once circulation has been completed the vapor return from the reboiler 190 to the tower 110 is reduced to ambient temperature or about ambient temperature and the system is drained of the cleaning solution.

As one of ordinary skill in the art may appreciate one or more steps may be omitted, and/or one or more steps may be added, to above method, and one or more elements may be added to or omitted from systems 100, 200, in the ordinary course of treating such systems without departing from the scope of the method.

EXAMPLES

In the examples below, cleaning solutions were tested for their ability to solubilize and mobilize foulant sludge (containing, for example, NMP degradation products, polymer binders such as polyvinylidene fluoride (PVDF), carbon deposits, and metal/metal oxide flakes) that accumulates in internal components of a system for the treatment of chemical waste streams for the purification and recovery of NMP.

Figure 3:
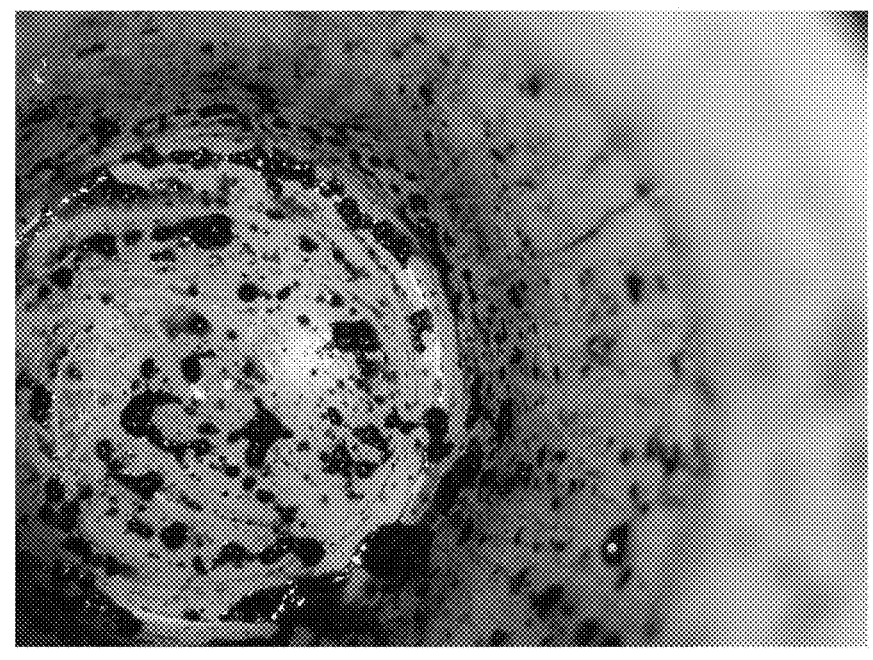
FIG. 3 is an image of an exemplary foulant sludge obtained from internal components of a system for the treatment of chemical waste streams for the purification and recovery of NMP.

FIG. 3 is an image of foulant sludge obtained from internal components of a system for the treatment of chemical waste streams for the purification and recovery of NMP.

Figure 4:
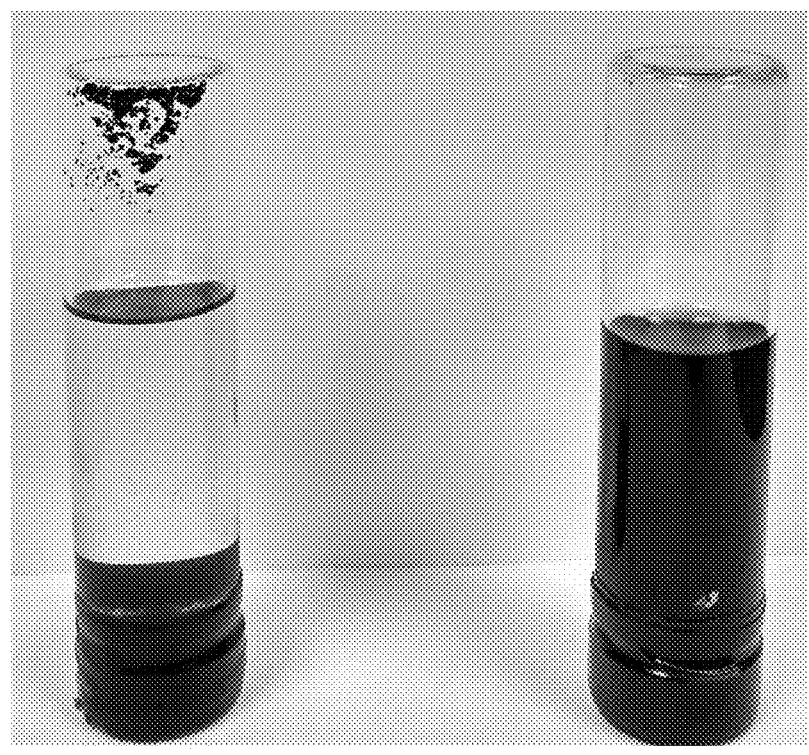
FIG. 4 is an image illustrating the foulant sludge solubilizing/mobilizing ability of Petroblast® (Terpenes-based cleaning solution, left vial) and neat diglycolamine (DGA, right vial) at room temperature.

Example 1—Solubilization/mobilization of foulant sludge using inventive cleaning solution and comparative prior art cleaning solution. 2-5 mg of foulant sludge was placed in each of two separate vials. To the first vial, 20 ml of PetroBlast® cleaning solution (a comparative cleaning solution made of 75-100 wt % natural terpenes and 0.1-10 wt % additive package), was added. To the second vial, 20 ml of neat diglycolamine (DGA, >98 wt %) was added. Both vials were stirred at room temperature. FIG. 4 is an image showing the foulant sludge solubilizing/mobilizing ability of PetroBlast® (left vial) and DGA (right vial). As shown in FIG. 4, the use of PetroBlast® appeared to only minimally solubilize the foulant sludge; fine solid particulates remained adhered to the glass vial indicating that PetroBlast® did not effectively solubilize and mobilize foulant particulates at room temperature. The inventors further noted that the use of PetroBlast® did not result in any additional solubilization of the foulant sludge after heating the vial to 220° C. for several days. In the vial containing neat DGA as the cleaning solution, on the other hand, the foulant sludge was effectively solubilized and mobilized at room temperature.

Example 2—Solubilization/mobilization of foulant sludge using inventive cleaning solution under various conditions. In this example, the ability of neat DGA (20 ml) to solubilize and mobilize foulant sludge (2-5 mg) under various conditions was tested. At room temperature (about 20° C.), greater than 50% of the foulant sludge was found to fully dissolve into neat DGA over a period of 24-72 hours with only occasional agitation (via shaking the vial by hand). At full reflux (about 220° C.) with glass boiling beads for only 10 minutes, greater than 99% of foulant sludge was found to dissolve. At 100° C. without agitation, greater than 99% of foulant sludge was found to dissolve after 45 minutes. In all experiments, the inventors observed that the neat DGA cleaning solution darkens from clear/slight yellow to a deep reddish-brown color over time.

Example 3—Solubilization/mobilization of foulant sludge using inventive cleaning solutions of varied DGA/water ratios at 55-60° C. In these examples, a series of solutions (Table 1) were prepared for foulant sludge solubility/mobility studies.

TABLE 1

| Cleaning Solution | DGA (w/w %) | Deionized (DI) water (w/w %) |
|---|---|---|
| 1 | >98 (neat) | 0 |
| 2 | 75 | 25 |
| 3 | 50 | 50 |
| 4 | 38 | 62 |
| 5 | 25 | 75 |
| 6 | 18 | 82 |
| 7 | 12 | 88 |
| 8 | 10 | 90 |
| 9 | 5 | 95 |

In this example, 2-5 mg of foulant sludge was placed in each of a plurality of a glass vials, each containing a magnetic stir bar. In a first foulant sludge-containing glass vial, 20 ml of cleaning solution #3 was added. In a second foulant sludge-containing glass vial, 20 ml of cleaning solution #5 was added. In a third foulant sludge-containing glass vial, 20 ml of cleaning solution #7 was added. In a fourth foulant sludge-containing glass vial, 20 ml of cleaning solution #9 was added. The vials were then placed in a water bath at 55-60° C. for 90 minutes with stirring. After 30-, 60- and 90-minute periods, the vials were removed from the water bath and qualitatively assessed for foulant solubility/mobility.

Figure 5:
FIG. 5 is an image illustrating, from left to right, the foulant sludge solubilizing ability of 50/50 w/w % DGA/ water, 25/75 w/w % DGA/water, 12/88 w/w % DGA/water, and 5/95 w/w % DGA/water cleaning solutions in accordance with various aspects of the present disclosure after 30 minutes at 55-60° C.

FIG. 5 is an image illustrating, from left to right, the resulting foulant-solubilized solutions using cleaning solutions #3, #5, #7 and #9, respectively, after a 30-minute period. As can be seen, after 30 minutes, cleaning solutions #3 and #5 solubilize the foulant sludge far more effectively than cleaning solutions #7 and #9.

Figure 6:
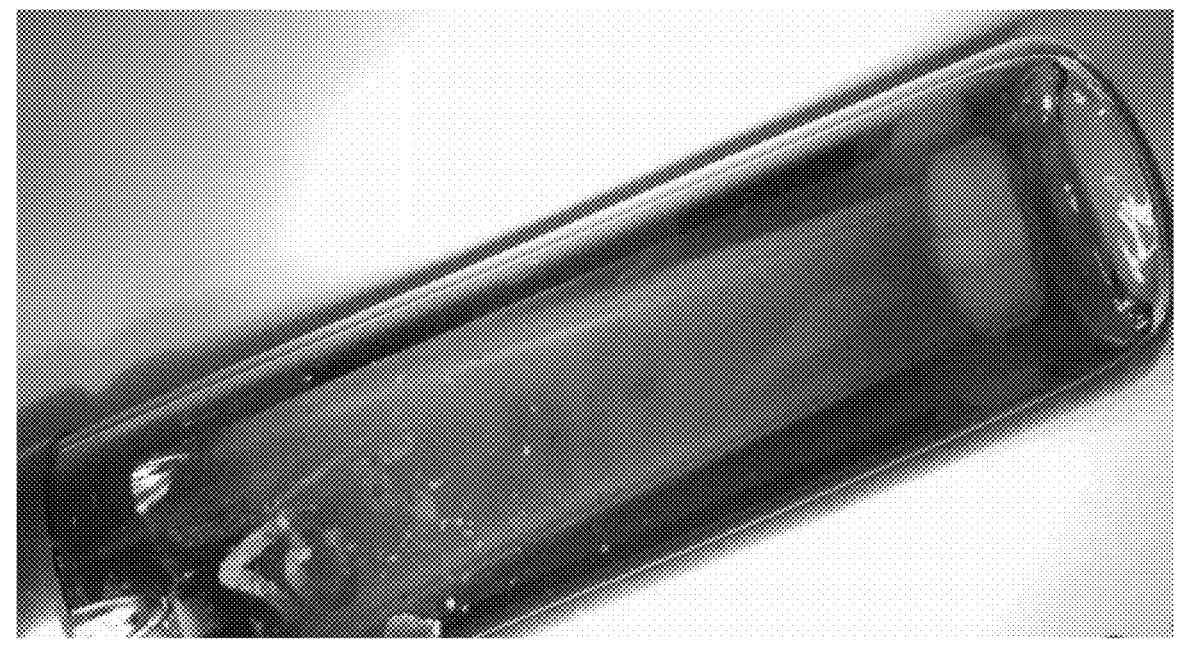
FIG. 6 is an image illustrating, from left to right, the foulant sludge solubilizing ability of a 50/50 w/w % DGA/ water cleaning solution in accordance with various aspects of the present disclosure after 90 minutes at 55-60° C.

FIG. 6 is an image illustrating the resulting foulant-solubilized solution using cleaning solution #3 after a 90-minute period. As can be seen, after 90 minutes, cleaning solution #3 solubilizes >99% of the foulant sludge. While not shown, similar dissolution capacity was observed for cleaning solutions #2 and #4.

Figure 7:
FIG. 7 is an image illustrating the resulting foulant-solubilized solution using a 25/75 w/w % DGA/water (left) and a 12/88 w/w % DGA/water (right) cleaning solution in accordance with various aspects of the present disclosure after 60 minutes at 55-60° C.

FIG. 7 is an image illustrating the resulting foulant-solubilized solution using cleaning solutions #5 (left) and #7 (right) after a 60-minute period. As can be seen, after 60 minutes, both solutions contain a number of undissolved particulates, but cleaning solution #7 has more than double the amount of undissolved particulates than observed in cleaning solution #5.

Figure 8:
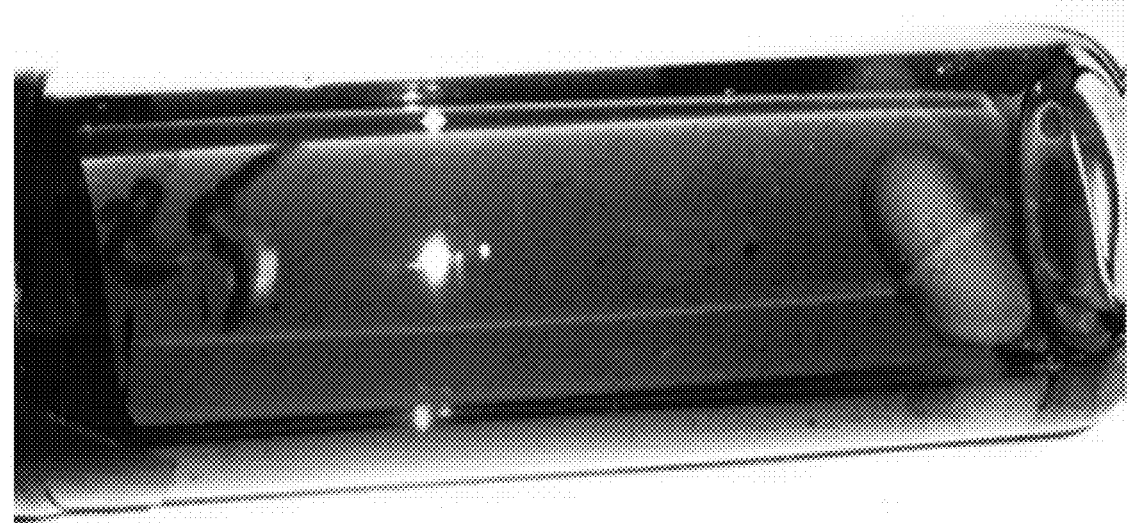
FIG. 8 is an image illustrating the resulting foulant-solubilized solutions using a 25/75 w/w % DGA/water cleaning solution in accordance with various aspects of the present disclosure after 90 minutes at 55-60° C.

FIG. 8 is an image illustrating the resulting foulant-solubilized solutions using cleaning solutions #5 after a 90-minute period. As can be seen, after 90 minutes, cleaning solution #5 exhibits good dissolution of the foulant sludge, with only a small amount of particulates suspended in solution.

Table 2 displays solubility test results of various experiments performed as described above.

TABLE 2

| Trial | DGA/water (w/w %) | Temp (° C.) | Time (min) | Dissolution (%) |
|---|---|---|---|---|
| 1 | neat DGA | 20 | 90 | Some |
| 2 | neat DGA | 60 | 90 | >99 |
| 3 | neat DGA | 100 | 45 | 100 |
| 4 | 75/25 | 60 | 90 | >99 |
| 5 | 50/50 | 60 | 90 | >99 |
| 6 | 38/62 | 60 | 90 | >90 |
| 7 | 25/75 | 60 | 90 | >75 |
| 8 | 18/82 | 60 | 90 | >50 |
| 9 | 12/88 | 60 | 90 | Some |
| 10 | 10/90 | 60 | 90 | No Significant change |
| 11 | 5/95 | 60 | 90 | No Significant change |
| 12 | 50/50 | 27 | 90 | Some |
| 13 | 50/50 | 35 | 90 | Some |
| 14 | 50/50 | 41 | 90 | Some |
| 15 | 50/50 | 49 | 90 | >75 |
| 16 | 50/50 | 60 | 90 | >99 |

Figure 9:
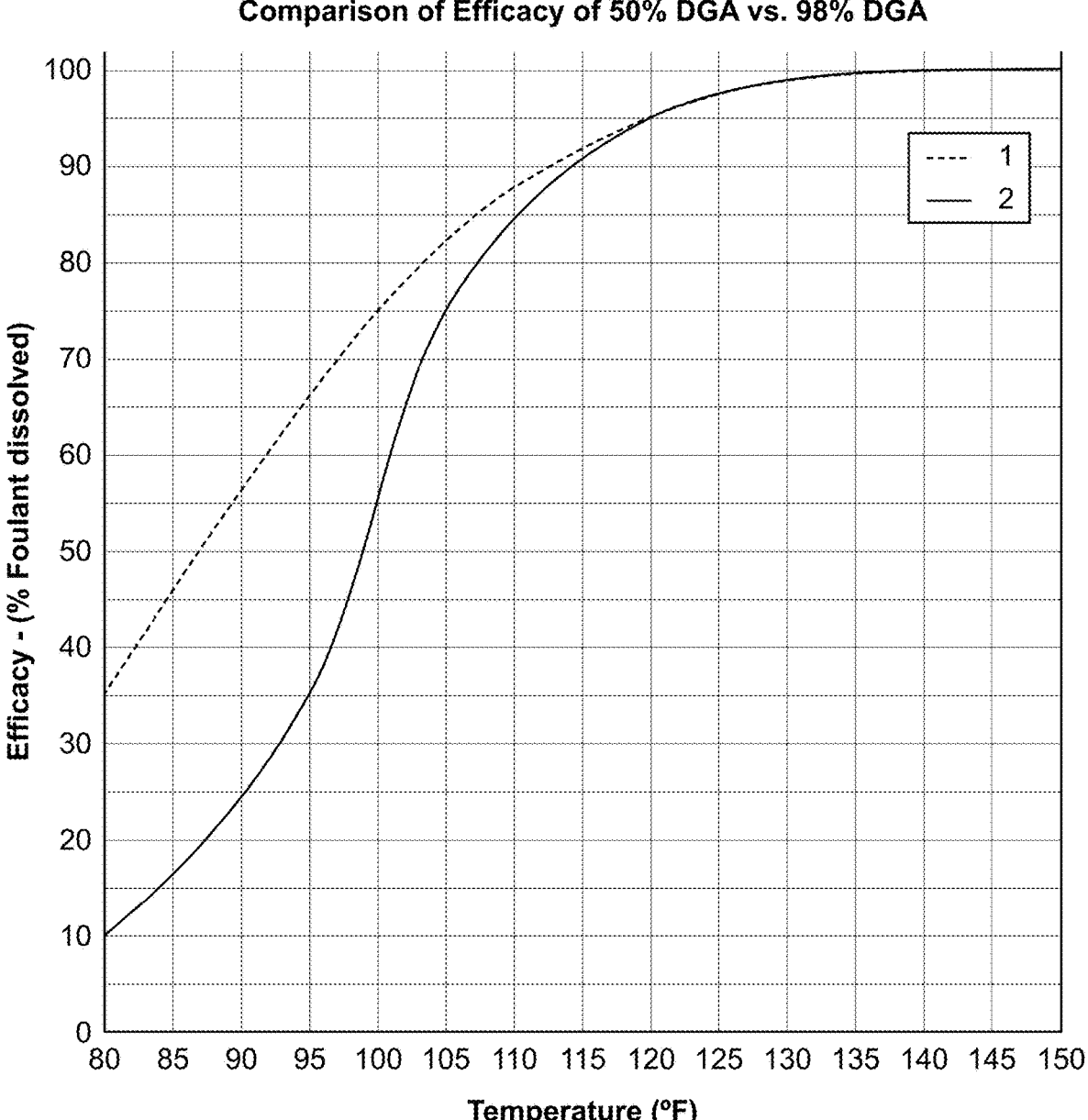
FIG. 9 is a graphical display illustrating the foulant sludge dissolution efficiency of (1) neat DGA and (2) 50/50 w/w % DGA/water cleaning solutions as a function of dissolution temperature.

Example 4—Comparing Solubilization/Mobilization of Foulant Sludge Using Neat DGA and 50/50 w/w % DGA/Water Cleaning Solutions at Varying Temperatures This example was performed according to example 3, except (1) neat DGA and (2) 50/50 w/w/% DGA/water cleaning solutions were evaluated as a function of dissolution temperature. The results of this example are shown graphically in FIG. 9. As can be seen, at lower operational temperatures (80 to about 115° F.) neat DGA has a higher dissolution efficiency than 50/50 w/w/% DGA/water. At higher operational temperatures (>115° F.) both solutions appear to exhibit substantially the same dissolution efficiency. In view of these results, the use of neat DGA would appear advantageous in systems at lower operational temperatures, while the use of 50/50 w/w % DGA/water would be advantageous at higher operational temperatures from the perspective of raw materials costs and DGA use minimization.

Although the present invention and its objects, features and advantages have been described in detail, other embodiments are encompassed by the invention. All references cited herein are incorporate by reference in their entireties. Finally, those skilled in the art should appreciate that they can readily use the disclosed conception and specific embodiments as a basis for designing or modifying other structures for carrying out the same purposes of the present invention without departing from the scope of the invention as defined by the appended claims.

What is claimed is:

1. A method of cleaning an N-methyl-2-pyrrolidone (NMP) purification and recovery system, the system comprising:
  an NMP-containing chemical waste stream;
  a separation tower fluidically coupled with the chemical waste stream;
  a reflux drum fluidically coupled with an upper section of the separation tower;
  a reboiler fluidically coupled with a lower section of the separation tower; and
  a purified NMP stream fluidically coupled with the reboiler;
  the method comprising:
  injecting a cleaning solution into the reflux drum and the reboiler with an amount of the cleaning solution sufficient to at least substantially fill the reflux drum and the reboiler, the cleaning solution comprising a solvent having a primary amine and a hydroxyl group;
  circulating the cleaning solution through at least the separation tower, the reflux drum, and the reboiler for a period of time to solubilize foulants contained within the system; and
  draining the cleaning solution having foulants solubilized therein from the system.

2. The method of claim 1, further comprising injecting the cleaning solution into the reflux drum and the reboiler with an amount of the cleaning solution sufficient to at least substantially fill a lower portion of the separation tower.

3. The method of claim 1, wherein circulating the cleaning solution is facilitated by a bottoms pump fluidically coupled with the lower section of the separation tower and the reboiler and an overhead pump fluidically coupled with the section of the separation tower and the reflux drum.

4. The method of claim 1, wherein a vapor return from the reboiler to the lower section of the separation tower is at ambient temperature prior to injecting the cleaning solution.

5. The method of claim 1, wherein a vapor return from the reboiler to the lower section of the separation tower is at an operating temperature of between about 38° C. and about 55° C. prior to injecting the cleaning solution.

6. The method of claim 1, wherein a vapor return from the reboiler to the lower section of the separation tower is at an operating temperature of between ambient temperature and about 55° C. prior to injecting the cleaning solution.

7. The method of claim 1, wherein a vapor return from the reboiler to the lower section of the separation tower is at an operating temperature of between about 38° C. and about 55° C. during circulation of the cleaning solution.

8. The method of claim 1, wherein the solvent is a glycolamine.

9. The method of claim 1, wherein the solvent is diglycolamine.

10. The method of claim 1, wherein the solvent is one or more of (2-aminoethoxy)ethanol, 2-[2-(2-aminoethoxy)ethoxy]ethanol, 2-(2-(2-(2-aminoethoxy)ethoxy)ethoxy) ethanol, 2-(2-amino-1-methylethoxy)ethanol, 2-[(3-amino-propyl)(ethyl)amino]ethanol, 2-(2-aminoethylamino) ethanol, 3-[(2-aminoethyl)amino]-1-propanol, and 2-(2-amino-1,1-dimethyl-ethylamino)ethanol.

11. The method of claim 1, wherein the cleaning solution has a solvent-to-water volumetric ratio ranging from about 50:50 to about 100:0.

12. The method of claim 1, wherein the cleaning solution has a water-to-solvent volumetric ratio ranging from about 80:20 to about 50.1:49.9.

13. The method of claim 1, wherein the period of time ranges from about 30 minutes to about 4 hours.

14. The method of claim 1, wherein the period of time ranges from about 1 hour to about 3 hours.

15. The method of claim 1, wherein the period of time is about 2 hours.

* * * * *